(12) United States Patent
Edwards

(10) Patent No.: US 7,326,207 B2
(45) Date of Patent: Feb. 5, 2008

(54) SURGICAL WEIGHT CONTROL DEVICE

(75) Inventor: Stuart D. Edwards, Portola Valley, CA (US)

(73) Assignee: Curon Medical, Inc., Hercules, CA (US)

( * ) Notice: Subject to any disclaimer, the term of this patent is extended or adjusted under 35 U.S.C. 154(b) by 154 days.

(21) Appl. No.: 11/043,902

(22) Filed: Jan. 26, 2005

(65) Prior Publication Data

US 2005/0183732 A1    Aug. 25, 2005

Related U.S. Application Data

(63) Continuation of application No. 09/571,080, filed on May 15, 2000, now abandoned.

(60) Provisional application No. 60/134,672, filed on May 18, 1999.

(51) Int. Cl.
*A61B 18/18* (2006.01)

(52) U.S. Cl. .................. 606/41; 606/32; 604/909; 607/40; 607/115; 607/116; 128/898

(58) Field of Classification Search .............. 606/41, 606/32; 604/909; 607/40, 115, 116; 128/898
See application file for complete search history.

(56) References Cited

U.S. PATENT DOCUMENTS

| | | | |
|---|---|---|---|
| 4,403,604 A | 9/1983 | Wilkinson et al. | |
| 4,592,339 A | 6/1986 | Kuzmak et al. | |
| 5,074,868 A | 12/1991 | Kuzmak | |
| 5,160,338 A | 11/1992 | Vincent | |
| 5,226,429 A | 7/1993 | Kuzmak | |
| 5,263,480 A | 11/1993 | Wernicke et al. | |
| 5,403,326 A | 4/1995 | Harrison et al. | |
| 5,472,441 A * | 12/1995 | Edwards et al. | 606/41 |
| 5,540,734 A | 7/1996 | Zabara | |
| 5,601,604 A | 2/1997 | Vincent | |
| 5,690,691 A | 11/1997 | Chen et al. | |
| 5,836,994 A | 11/1998 | Bourgeois | |
| 5,957,920 A | 9/1999 | Baker | |

(Continued)

FOREIGN PATENT DOCUMENTS

EP    0 334 086    9/1989

(Continued)

*Primary Examiner*—Michael Peffley
*Assistant Examiner*—Victoria W. Chen
(74) *Attorney, Agent, or Firm*—Ryan Kromholz & Manion, S.C.

(57) ABSTRACT

This invention provides a method and system for the curative treatment of obesity. A first aspect of this invention is that it enables identification of the nerves responsible for the relaxation of the stomach muscles that occurs prior to and during eating. A second aspect of the invention is that it allows the physician to identify focal nerve sites in the stomach and upper duodenum that are associated with producing sensations of hunger and satiety. Nervous transmission from these sites can be modulated or blocked all together so as to minimize the sensation of hunger. A third aspect of this invention is that allows a physician to shrink selected portions of the innermost oblique muscle and middle circular muscle layers of the stomach. This can be performed in a physician's office using local anesthesia. Shrinkage of these muscles produces a feeling of satiety that enhances the patient's efforts to restrict his caloric intake.

6 Claims, 5 Drawing Sheets

U.S. PATENT DOCUMENTS

| | | | |
|---|---|---|---|
| 6,006,755 A | 12/1999 | Edwards | |
| 6,014,579 A | 1/2000 | Pomeranz et al. | |
| 6,044,846 A | 4/2000 | Edwards | |
| 6,056,744 A | 5/2000 | Edwards | |
| 6,077,257 A | 6/2000 | Edwards et al. | |
| 6,092,528 A | 7/2000 | Edwards | |
| 6,197,022 B1 | 3/2001 | Baker | |
| 6,212,433 B1* | 4/2001 | Behl | 607/101 |
| 6,254,598 B1* | 7/2001 | Edwards et al. | 606/41 |
| 6,258,087 B1* | 7/2001 | Edwards et al. | 606/41 |
| 6,273,886 B1* | 8/2001 | Edwards et al. | 606/34 |
| 6,325,798 B1* | 12/2001 | Edwards et al. | 606/41 |
| 6,355,031 B1* | 3/2002 | Edwards et al. | 606/31 |
| 6,358,245 B1* | 3/2002 | Edwards et al. | 606/34 |
| 6,363,937 B1* | 4/2002 | Hovda et al. | 128/898 |
| 6,402,744 B2* | 6/2002 | Edwards et al. | 606/41 |
| 6,405,732 B1 | 6/2002 | Edwards et al. | |
| 6,419,673 B1 | 7/2002 | Edwards et al. | |
| 6,423,058 B1* | 7/2002 | Edwards et al. | 606/41 |
| 6,427,089 B1 | 7/2002 | Knowlton | |
| 6,440,128 B1* | 8/2002 | Edwards et al. | 606/41 |
| 6,464,689 B1 | 10/2002 | Qin et al. | |
| 6,464,697 B1* | 10/2002 | Edwards et al. | 606/41 |
| 6,540,789 B1 | 4/2003 | Silverman et al. | |
| 6,544,226 B1 | 4/2003 | Gaiser et al. | |
| 6,547,776 B1 | 4/2003 | Gaiser et al. | |
| 6,558,400 B2 | 5/2003 | Deem et al. | |
| 6,589,238 B2 | 7/2003 | Edwards et al. | |
| 6,645,201 B1 | 11/2003 | Utley et al. | |
| 6,699,243 B2 | 3/2004 | West et al. | |
| 6,733,495 B1 | 5/2004 | Bek et al. | |
| 6,783,523 B2 | 8/2004 | Qin et al. | |
| 6,790,207 B2 | 9/2004 | Utley et al. | |
| 6,802,841 B2 | 10/2004 | Utley et al. | |
| 6,827,713 B2 | 12/2004 | Bek et al. | |
| 2002/0013581 A1* | 1/2002 | Edwards et al. | 606/41 |
| 2002/0028979 A1 | 3/2002 | Silverman et al. | |
| 2002/0072738 A1* | 6/2002 | Edwards et al. | 606/41 |
| 2002/0082670 A1 | 6/2002 | Utley et al. | |
| 2002/0115992 A1 | 8/2002 | Utley et al. | |
| 2002/0139379 A1 | 10/2002 | Edwards et al. | |
| 2002/0151871 A1 | 10/2002 | Gaiser et al. | |
| 2002/0162555 A1 | 11/2002 | West et al. | |
| 2002/0183735 A1 | 12/2002 | Edwards et al. | |
| 2003/0023287 A1 | 1/2003 | Edwards et al. | |
| 2003/0144708 A1 | 7/2003 | Starkebaum | |
| 2003/0153905 A1 | 8/2003 | Edwards et al. | |
| 2004/0089313 A1 | 5/2004 | Utley et al. | |
| 2004/0215180 A1* | 10/2004 | Prentice et al. | 606/41 |
| 2006/0247718 A1* | 11/2006 | Starkebaum | 607/40 |

FOREIGN PATENT DOCUMENTS

| | | |
|---|---|---|
| EP | 0 571 938 A2 | 12/1993 |
| WO | WO 00/69376 | 11/2000 |
| WO | WO 02/11696 | 2/2002 |
| WO | WO 02/13854 | 2/2002 |
| WO | WO 02/053040 | 7/2002 |

* cited by examiner

SURGICAL WEIGHT CONTROL DEVICE

RELATED APPLICATIONS

This application is a continuation of U.S. application Ser. No. 09/571,080, filed May 15, 2000, now abandoned which claims the benefit of provisional U.S. Application Ser. No. 60/134,672, filed May 18, 1999.

FIELD OF THE INVENTION

This invention relates to controlling obesity.

BACKGROUND OF THE INVENTION

Obesity is directly associated with disorders such as osteoarthritis (especially in the hips) sciatica, varicose veins, thromboembolism, ventral and hiatal hernias, hypertension, insulin resistance and hyperinsulinemia. All of these conditions can be ameliorated by treatment of obesity, provided the weight loss is significant and enduring.

The known art of treating obesity includes behavioral strategies, various different pharmaceutical interventions and surgery.

One problem in the known art of behavioral strategies is patient compliance. Extremely high levels of patient compliance over a long period of time are required to produce a significant weight loss.

Problems in the known art of pharmaceutical intervention include drug dependence and side effects. Treatment with amphetamine analogs requires habitual use of an addictive drug to produce a significant weight loss. Treatment with drugs such dexfenfluramine and fenfluramine is frequently associated with primary pulmonary hypertension and cardiac valve abnormalities. Drugs such as sibutramine cause a substantial increase in blood pressure in a large number of patients.

The known art of surgical treatment of obesity includes operative procedures such as end-to-end anastomosis of about 38 cm of proximal jejunum to 10 cm of terminal ileum and other variants of jejunoileal manipulation. While such procedures are extremely effective, the overall rates of surgical mortality and associated hepatic dysfunction are so high that this treatment is only indicated for younger patients who are morbidly obese.

Accordingly, it would be advantageous to provide a method and system for treatment of obesity that produces reasonably rapid weight loss, long term results, low surgical mortality, few side effects and can be performed under local anesthesia. This advantage is achieved is an embodiment of an invention in which a balloon bearing an array of electrodes is deployed in the stomach and upper duodenum. This device maps and ablates nerves in these tissues and causes shrinkage of stomach muscle by creating a pattern of thermal lesions. Weight control is achieved by creating a sense of satiety in the patient. This can be achieved by direct modulation of nerves responsible for the sensation of hunger or by inhibiting the let-down reflex of the stomach muscles that serves as a precursor to digestion.

SUMMARY OF THE INVENTION

This invention provides a method and system for the curative treatment of obesity.

A first aspect of this invention is that it enables identification of the nerves responsible for the relaxation of the stomach muscles that occurs prior to and during eating. Relaxation and extension of these muscles allows the stomach to take in a greater quantity of food and facilitates the feeding process. In the event that impulses from the gastric cardia fail to transmit information to the vagus nerve and hindbrain, the muscular tone of the stomach will remain normal during a meal. The result is early satiety and correspondingly, less food intake. In a preferred embodiment, this invention can be used to modulate these nerves in the gastric cardia and inhibit the relaxation of stomach muscles, thereby creating a sensation of fullness more rapidly than would occur otherwise.

A second aspect of the invention is that it allows the physician to identify focal nerve sites in the stomach and upper duodenum that are associated with producing sensations of hunger and satiety. Nervous transmission from these sites can be modulated or blocked all together so as to minimize the sensation of hunger.

A third aspect of this invention is that it allows a physician to shrink selected portions of the innermost oblique muscle and middle circular muscle layers of the stomach. This can be performed in a physician's office using local anesthesia. Shrinkage of these muscles produces a feeling of satiety that enhances the patient's efforts to restrict his caloric intake.

One method provides for delivering energy to ablate tissue in a least one of the stomach, duodenum, and gastric cardia. Ablating tissue creates a thermal lesion that causes shrinkage of stomach muscle. In one embodiment, the method further comprises, prior to delivering energy, identifying nerves responsible for relaxation of stomach muscles. Delivering energy can serve to modulate nerves in the gastric cardia to inhibit the relaxation of stomach muscles. In one embodiment, energy is delivered to portions of the duodenum that are generally proximate to the stomach. In one embodiment, the energy delivered is radio frequency energy.

An apparatus for treatment of obesity comprises a catheter capable of being disposed proximate to a junction between the stomach and the duodenum of a patient, a first balloon, a second balloon, a plurality of electrodes embedded in the outer surfaces of said first balloon and said second balloon, and a plurality of lumens. The catheter can be disposed in the gastric cardia, greater curvature, collar of helvetius, middle circular stomach muscle layers, longitudinal and circular muscles of the duodenum, the pylorus, and other structures proximate to the stomach. The catheter is sized and configured to be inserted orally or through a surgical opening. The length of the catheter is responsive to the relative size or age of the patient and the manner of insertion.

The first and second treatment balloons may be comprised of kevlar, mylar, or any biologically non-reactive polymer. The first and second treatment balloons may include a plurality of micropores that can be used for delivery of irrigating fluids, chilling liquids or pharmaceutical agents. The first and second treatment balloons are capable of being expanded so as to be in proximity of the interior of a stomach, duodenum or organs adjacent thereto, such as the pylorus. The first and second treatment balloons include at least one localized receiver that is responsive to the potential of a nerve, impedance, temperature, current or voltage.

The plurality of electrodes may include a set of needle-like electrodes. In one embodiment, the plurality of needle-like electrodes is arced. In one embodiment, each electrode includes a thermocouple. The transmission of energy from each electrode may be responsive to feedback from the thermocouple.

In one embodiment, the electrodes are disposed to deliver radio frequency energy. The electrodes may also be disposed to deliver infrared light, microwave, ultrasound, electromagnetic, photodynamic therapy, or other forms of energy.

In one embodiment, the apparatus includes a spacer so as to separate the first and second balloons in such a way that the first balloon delivers energy and liquids to the duodenum and the second balloon delivers energy and substances to a location in the stomach simultaneously or sequentially.

In one embodiment, lumens conduct liquid or energy to and from a source external to the patient and a targeted portion of the interior of a stomach, duodenum and pylorus.

An alternative apparatus for treatment of obesity includes a catheter capable of being disposed proximate to a junction between the stomach and the duodenum, a treatment balloon, a set of struts, a plurality of electrodes embedded in said set of struts, and a plurality of lumens. The catheter can be disposed, either by oral insertion or through a surgical opening, proximate to a gastric cardia, greater curvature, collar of helvetius, middle circular stomach muscle layers, longitudinal and circular muscles of the duodenum, the pylorus, and other structures in the digestive system.

The length of the catheter may be responsive to the relative age or size of the patient and the manner of insertion. The treatment balloon may be comprised of kevlar, mylar, or any biologically non-reactive polymer.

The treatment balloon may include a plurality of micropores that can be used for delivery of irrigating fluids, chilling liquids, or pharmaceutical agents. The treatment balloon may be capable of being expanded so as to cause the plurality of struts to be in immediate proximity to the interior of a stomach, duodenum, or organs adjacent thereto. The set of struts may encompass the exterior surface of the treatment balloon in such a way that expansion of the balloon causes outward movement of said struts.

The electrodes may have at least one localized receiver that is responsive to the potential of a nerve, impedance, temperature, current, or voltage. The plurality of electrodes may include a set of needle-like electrodes. In one embodiment, the set of needle-like electrodes is arced. In one embodiment, each electrode in includes a thermocouple. The transmission of energy from each electrode may be responsive to feedback from the thermocouple. In one embodiment, the electrodes are disposed to deliver radio frequency energy. The electrodes may also be disposed to deliver infrared light, microwave, ultrasound, electromagnetic, photodynamic therapy, or other forms of therapeutic energy.

In one embodiment, lumens conduct liquid or energy to and from a source external to the patient and a targeted portion of the interior of a stomach, duodenum, pylorus, or associated structure.

A method is provided for treatment of obesity which includes inserting a catheter, either orally or through a surgical opening, into the stomach of a patient, identifying particular nervous tissue and other structures within the stomach and associated structures, inflating a first treatment balloon, inflating a second treatment balloon, and deploying at least one electrode in a tissue.

Nervous tissue may be identified by visual inspection, measurement of nervous potential or impedance, or by other means.

The first and second treatment balloons may be inflated with a chilled liquid, an irrigating liquid or a pharmaceutical agent. The chilled liquid, irrigating fluid, or pharmaceutical agent may be delivered to a tissue included in the stomach or duodenum through micropores in the first or second balloon.

Deploying the at least one electrode may include creating thermal or other lesions in a stomach, duodenum, pyloris, or associated structures. Deploying the electrode may also include starting the flow of energy into a tissue through the electrode in response to feedback from a thermocouple or other sensor. Deploying the electrode may also include ablating a nerve so as to inhibit the relaxation of a stomach muscle. Deploying the electrode may also include delivering microwave, radio frequency, laser, infrared, ultrasound, or other therapeutic energy to the interior of a stomach, duodenum, or pylorus.

Another method for treatment of obesity, includes inserting a catheter, either orally or through a surgical opening, into the stomach of a patient, identifying particular nervous tissue and other structures within the stomach and associated structures, inflating a treatment balloon in such a way that at least one strut is positioned relatively proximate to the interior wall of a stomach or a duodenum, and deploying at least one electrodes in a tissue.

Nervous tissue may be identified by visual inspection, measurement of nervous potential or impedance, or by other means.

The treatment balloon may be inflated with a chilled liquid, an irrigating liquid or a pharmaceutical agent. The chilled liquid, irrigating fluid, or pharmaceutical agent may be delivered to a tissue included in the stomach or duodenum through micropores in the treatment balloon.

Deploying the at least one electrode may include creating thermal or other lesions in a stomach, duodenum, pyloris, or associated structures. Deploying the electrode may also include starting the flow of energy into a tissue through the electrode in response to feedback from a thermocouple or other sensor. Deploying the electrode may also include ablating a nerve so as to inhibit the relaxation of a stomach muscle. Deploying the electrode may also include delivering microwave, radio frequency, laser, infrared, ultrasound, or other therapeutic energy to the interior of a stomach, duodenum, or pylorus.

DETAILED DESCRIPTION OF THE PREFERRED EMBODIMENT

In the following description of a preferred embodiment of the invention is described with regard to preferred process steps and data structures. Those skilled in the art would recognize, after perusal of this application, that embodiments of the invention can be implemented using circuitry or other structures adapted to particular process steps and data structures, and that implementation of the process steps and data structures described herein would not require undue experimentation or further invention.

System Elements

Figure 1:
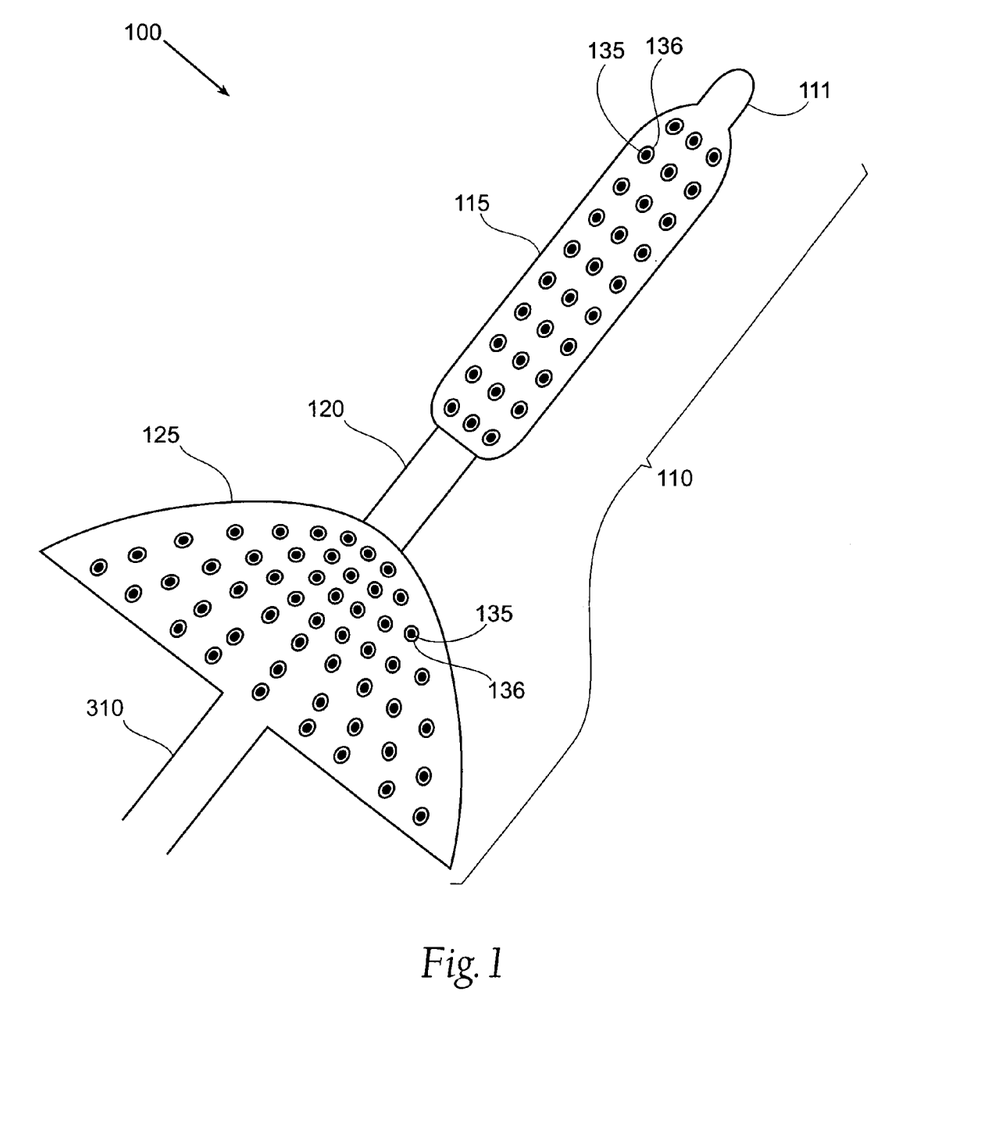
FIG. 1 is a block diagram of a first device used in a system for treatment of obesity.

FIG. 1 is a block diagram of a first device used in a system for treatment of obesity.

A system 100 includes a treatment element 110, a catheter 310 and a control apparatus 315. The treatment element 110 is mounted on the most distal end of the catheter 310 in such a way that the treatment element 110 and catheter 310 form one contiguous piece. This Figure is restricted to the treatment element 110. The catheter 310 and control apparatus 315 are described in greater detail in FIG. 3.

The treatment element 110 includes a distal tip 111, a first balloon 115, a spacer 120, a second balloon 125, and a plurality of lumens (not shown). Both the first balloon 115 and second balloon 125 include a set of electrodes 135 and a set of thermocouples 136.

The distal tip 111 is composed of a long, relatively narrow tubular element composed of relatively stiff, biologically non-reactive plastic that is disposed for insertion into the stomach and the portion of the duodenum immediately proximate to the stomach. In a preferred embodiment, the distal tip 111 is an extension of the catheter 310 (described supra).

The first balloon 115 is mounted between the distal tip 111 and the spacer 120. In a preferred embodiment, the first balloon 115 is approximately three times as long as it is wide, with the long end running between the distal tip 111 and the spacer 120. The walls of the first balloon 115 are comprised of mylar or a similar biologically non-reactive material that can be inflated with a variety of liquids such as saline, Ringers or water. In some embodiments, the first treatment balloon 115 includes micropores for delivery of liquid to a tissue. In these embodiments, pharmacological agents such as irrigating fluids, antibiotics, anti-inflammatories, anti-spasmodics and anesthetics can be exuded from micropores in the balloon 115. Some of the lumens included in the plurality of lumens are dedicated to inflation and deflation of the first balloon 115.

The electrodes 135 are distributed equidistant to each other in concentric rings along a longitudinal axis of the first treatment balloon 115. Each electrode 135 includes a thermocouple 136 so that the temperature of each electrode 135 can be monitored separately.

In a preferred embodiment, the electrodes 135 included in the first balloon 115 are disposed to deliver RF energy to portions of the duodenum that are generally proximate to the stomach. In other embodiments, the electrodes 135 may be disposed to deliver microwave, laser, ELF (extremely low frequency) or other therapeutic energies.

A spacer 120 lies between the first treatment balloon 115 and the second treatment balloon 125. In a preferred embodiment, the spacer 120 lies in the same plane as the distal tip 115 and is composed of relatively stiff material comparable to that of the distal tip 115 and catheter. Although the size of the spacer 120 may vary (for example, a spacer 120 used in a device to treat children will be smaller than a spacer 120 used in a device to treat adults), the relative proportions between the spacer 120 and the size of the first and second treatment balloons 115 and 125 do not vary.

In a preferred embodiment the spacer 120 separates the first treatment balloon 115 and second treatment balloon 125, thereby allowing two separate and distinct areas (that is, areas in the duodenum and stomach) to be treated individually and simultaneously.

The second treatment balloon 125 is mounted between the spacer 120 and the catheter 310 and control apparatus 315. In a preferred embodiment, the shape of the second balloon 125 is similar to a bisected sphere with the center of the spherical side coupled to the spacer 120 and the flat portion coupled to the catheter 310. The widest portion of the second treatment balloon 125 is approximately three times wider than the width of the first treatment balloon 120. In a preferred embodiment, the second treatment balloon 125 is disposed in a stomach while the first treatment balloon 115 is disposed in a duodenum.

Similar to the first treatment balloon 115, the second treatment balloon 125 is comprised of mylar or other similar biologically non-reactive material that can be inflated with air or a variety of liquids such as saline, Ringers or water. In some embodiments of the invention, the second treatment balloon 125 includes micropores for delivery of a liquid to a tissue. In these embodiments, pharmacological agents such as irrigating fluids, antibiotics, anti-inflammatories, anti-spasmodics and anesthetics may be exuded from micropores in the balloon 125. Some of the lumens included in the plurality of lumens 140 are dedicated to inflation and deflation of the second balloon 125.

The electrodes 135 are distributed equidistant to each other in concentric rings along a spherical portion of the second treatment balloon 115. There are no electrodes 135 on the proximal side of the second treatment balloon 125 (that is, the portion of the balloon 125 coupled to the catheter 310 and control apparatus 315). Each electrode 135 includes a thermocouple 136 so that the temperature of each electrode 135 can be monitored separately.

In a preferred embodiment, the electrodes 135 included in the second balloon 125 are disposed to deliver RF energy to portions of the stomach, in other embodiments, the electrodes 135 may be disposed to deliver microwave, laser, ELF (extremely low frequency) or other therapeutic energies.

The lumens are disposed to control the electrodes 135, transmit the RF energy or channel the fluids to the first treatment balloon 115 and the second treatment balloon 125. All of the lumens traverse the entire length of the catheter 310 and terminate at the treatment element 110 at an electrode 135, a thermocouple 136, the interior of a first treatment balloon 115 or the interior of a second treatment balloon 125.

Figure 2:
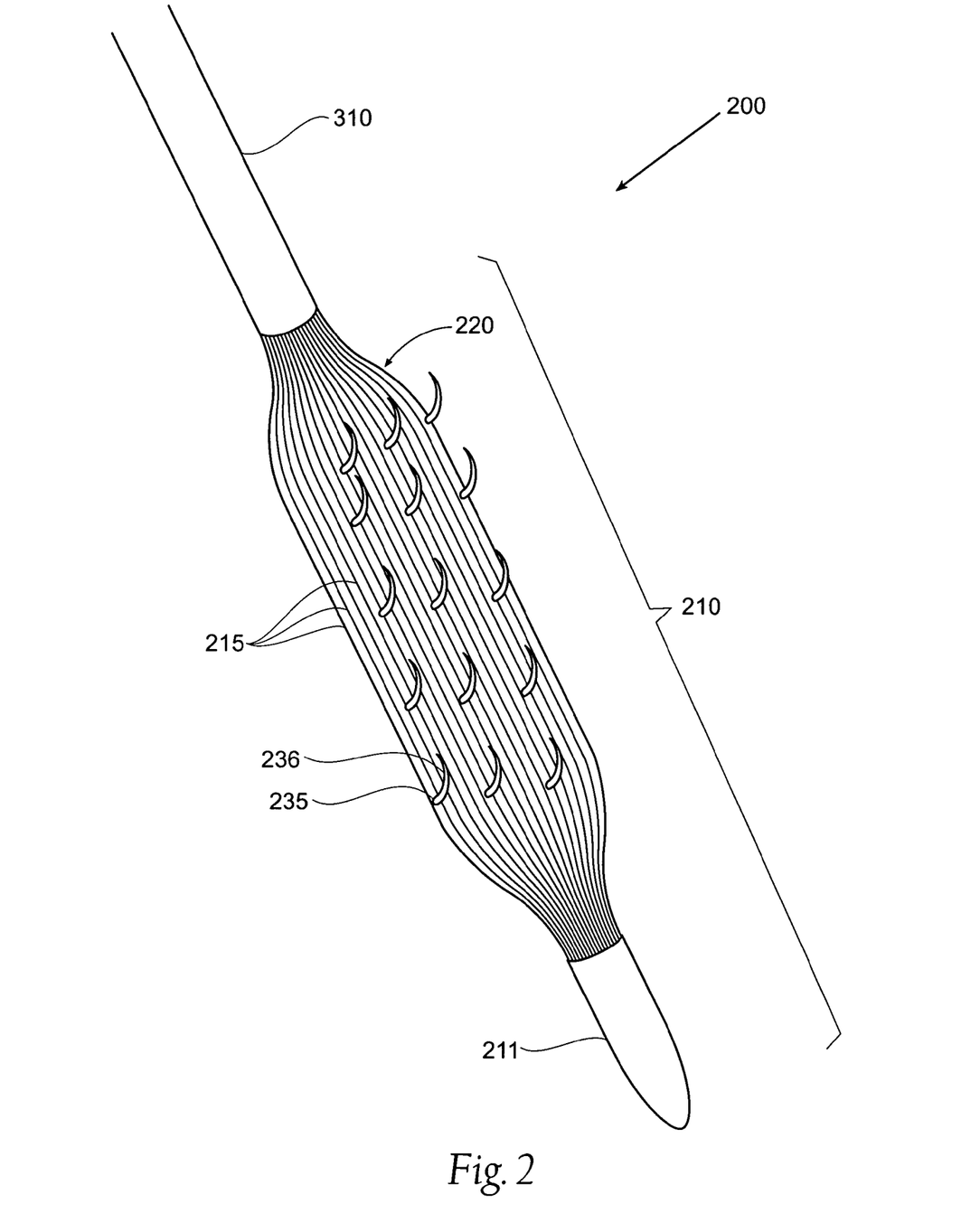
FIG. 2 is a block diagram of a second device used in a system for treatment of obesity.

FIG. 2 is a block diagram of a second device used in a system for treatment of obesity.

A system 200 includes a treatment element 210, a catheter 310 and a control apparatus 315. The treatment element 210 is mounted on the most distal end of the catheter 310 in such a way that the treatment element 210 and catheter 310 form one contiguous piece. FIG. 2 is restricted to the treatment element 210. The catheter 310 and control apparatus 315 are described in greater detail in FIG. 3.

The treatment element 210 includes a distal tip 211, a plurality of struts 215, a balloon 220 and a plurality of lumens (not shown). The set of struts 215 includes a set of electrodes 235 and a set of thermocouples 236.

The distal tip 211 is composed of a long, relatively narrow tubular element composed of relatively stiff, biologically non-reactive plastic that is disposed for insertion into the stomach and the portion of the duodenum immediately proximate to the stomach. In a preferred embodiment, the distal tip 211 is an extension of the catheter 310 (described supra).

The plurality of struts 215 is mounted between the distal tip 211 and catheter so that the distal end of each strut terminates at the proximal end of the distal tip 211 and the proximal end of each strut terminates at the catheter 310. The length of struts included in the plurality of struts 215 between the distal tip 211 and catheter is between three and four times as long as the distal tip 211. In a preferred embodiment, there are between ten and twenty individual struts 215. Other embodiments may include different numbers of struts 215.

Each strut in the plurality of struts 215 includes at least one electrode from the plurality of electrodes 235. Each electrode 235 includes a thermocouple 236 so that the temperature of each electrode 235 can be monitored separately. The electrodes 235 are slightly arced needle electrodes, mounted in such a way as to curve away from the distal tip 211. Each electrode 235 is staggered along the length of the strut 215 relative to the other electrodes 235 so that taken together, the plurality of electrodes 235 are evenly distributed at different lengths along the struts 215.

In a preferred embodiment, the electrodes 235 are disposed to deliver RF energy to the stomach and portions of the duodenum that are generally proximate to the stomach. In other embodiments, the electrodes 235 may be disposed to deliver microwave, laser, ELF (extremely low frequency) or other therapeutic energies. The electrodes 235 may also be disposed to deliver a variety of substances such as cooling liquids and pharmaceutical agents.

In addition to the struts 215, a balloon 220 is also mounted between the distal tip 215 and the catheter 310. The balloon 220 is coupled in such a way that the exterior portion of the balloon 220 is encircled by the set of struts 215. Inflation of the balloon 220 causes the electrodes 235 to be brought into closer proximity to the targeted tissue in the duodenum and stomach. In a preferred embodiment, the balloon 220 can be inflated with a variety of cooling liquids such as saline, Ringers or water. In other embodiments, the balloon 220 includes a plurality of micropores. In such embodiments, pharmacological agents such as irrigating fluids, antibiotics, anti-inflammatories, anti-spasmodics and anesthetics can be exuded from micropores in the balloon. Some of the lumens included in the plurality of lumens are dedicated to inflation and deflation of the balloon 220.

The lumens are disposed to control the electrodes 235, transmit the RF energy or channel the fluids to the treatment balloon 220. All of the lumens 130 traverse the entire length of the catheter 310 and terminate at the treatment element 210 either at an electrode 235, a thermocouple 236 or in the interior of a treatment balloon 220.

Figure 3:
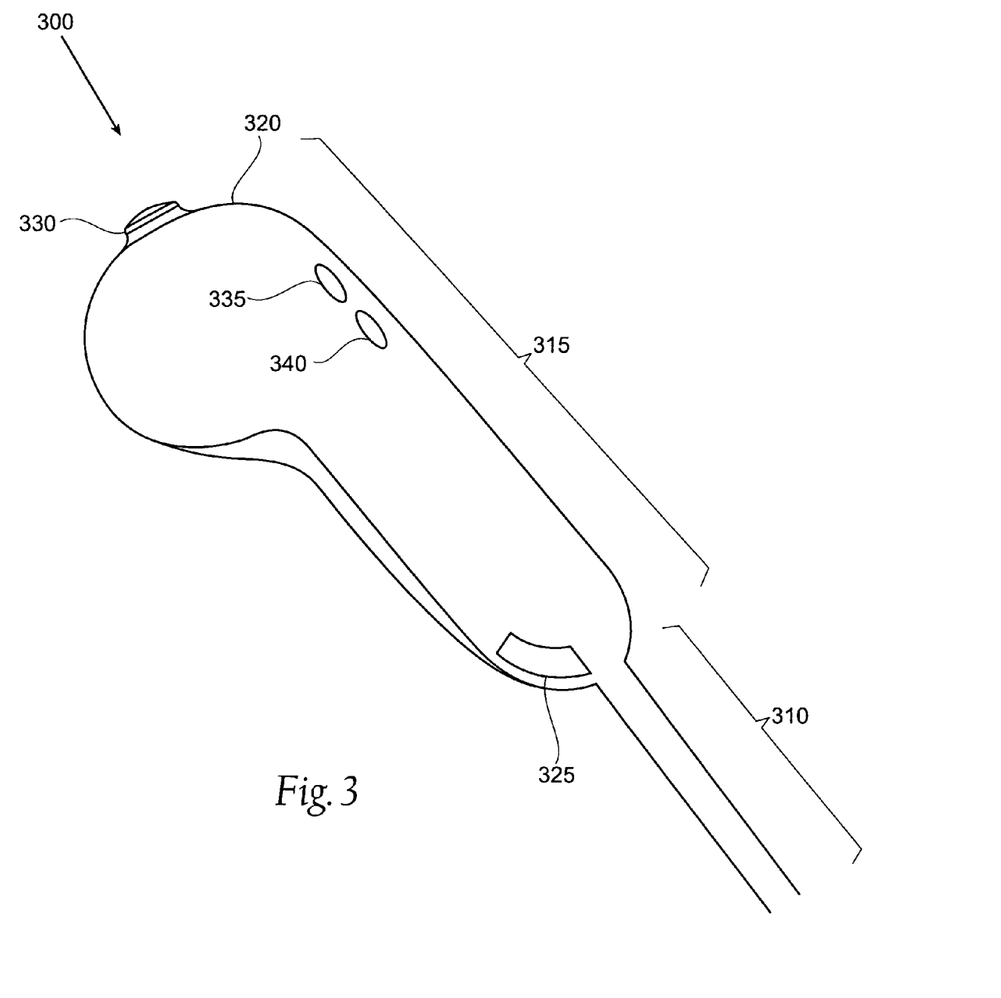
FIG. 3 is a block diagram of a control apparatus to be used with a first or second device in a system for treatment of obesity.

FIG. 3 is a block diagram of a control apparatus to be used with a first or second device in a system for treatment of obesity.

A system 300 is used to control the delivery of energy, cooling fluids and pharmaceutical agents through the first and second devices described infra.

A system 300 includes a catheter 310 and control mechanism 315. The control mechanism 315 houses all the elements needed to control the treatment element 110 or treatment element 210. As such, the control mechanism 315 includes a handgrip 320, an electrode manipulation element 325, a therapeutic energy connector 330, an inflation control port 335 and a deflation control port 340.

The catheter 310 is coupled on the distal end to treatment element 110 or treatment element 210 and coupled on the proximal end to the control mechanism 315. The catheter 310 is comprised of biologically non-reactive material and is sufficiently flexible so as to be introduced through the oral cavity, threaded through an esophagus and into a stomach. The overall length of the catheter may vary, but is responsive to the distance from a mouth to a duodenum. In alternative embodiments, the overall length of the catheter 310 may be responsive to the distance between a surgical incision and a duodenum. The catheter 310 is disposed to house lumens (not shown), which traverse the entire length of the catheter 310.

The electrode manipulation element 325 is mounted on the most distal portion of the control apparatus 325 immediately adjacent and contiguous with the handgrip 320. The electrode manipulation element 325 is coupled to proximal end of some of the lumens 140. As such, the electrode manipulation element 325 can be used to activate or deactivate electrodes included in systems 100 or 200. These electrodes can be controlled either individually or in combination. Activation or deactivation is also responsive to feedback from thermocouples 136 or 236 or to the physician's professional judgment.

The therapeutic energy connector 330 is mounted on the most proximal end of the control apparatus 325. As such, it is coupled to the most proximal end of some of the lumens 140 or 240 that traverse the interior of the catheter 310 and handgrip 320. In a preferred embodiment, the therapeutic energy connector 330 is disposed to be connected to an RF generator. In other embodiments, the therapeutic energy connector 330 can be disposed to be connected to a generator of microwaves, infrared, ELF, laser or other therapeutic energy.

The inflation control port 335 is mounted immediately between the therapeutic energy connector 330 and the deflation control port 340 on the top portion of the control apparatus 325. The proximal end of some of the lumens terminate at the inflation control port 325.

In a preferred embodiment, the inflation control port 335 is disposed to be coupled to a source of cooling liquids or pharmaceutical agents in liquid form. Examples of substances that can be introduced through the fluid input port 335 include sterile saline, sterile water, Ringers, antibiotic solutions, local anesthetics and other agents.

Deflation control port 340 is immediately adjacent to the inflation control port 335. The interior portion of the deflation control port 340 is coupled to some of the lumens in such a way that fluids used to inflate the first treatment balloon 115, second treatment balloon 125 or treatment balloon 220 can be suctioned away and the balloons deflated.

In a preferred embodiment the fluid output port 340 may be coupled to a pump or other apparatus to remove fluids. Pumping may occur in response to liquids entering the inflation control port 335, so as to achieve a continuously circulating stream of cooling liquid.

Method of Use

Figure 4A:
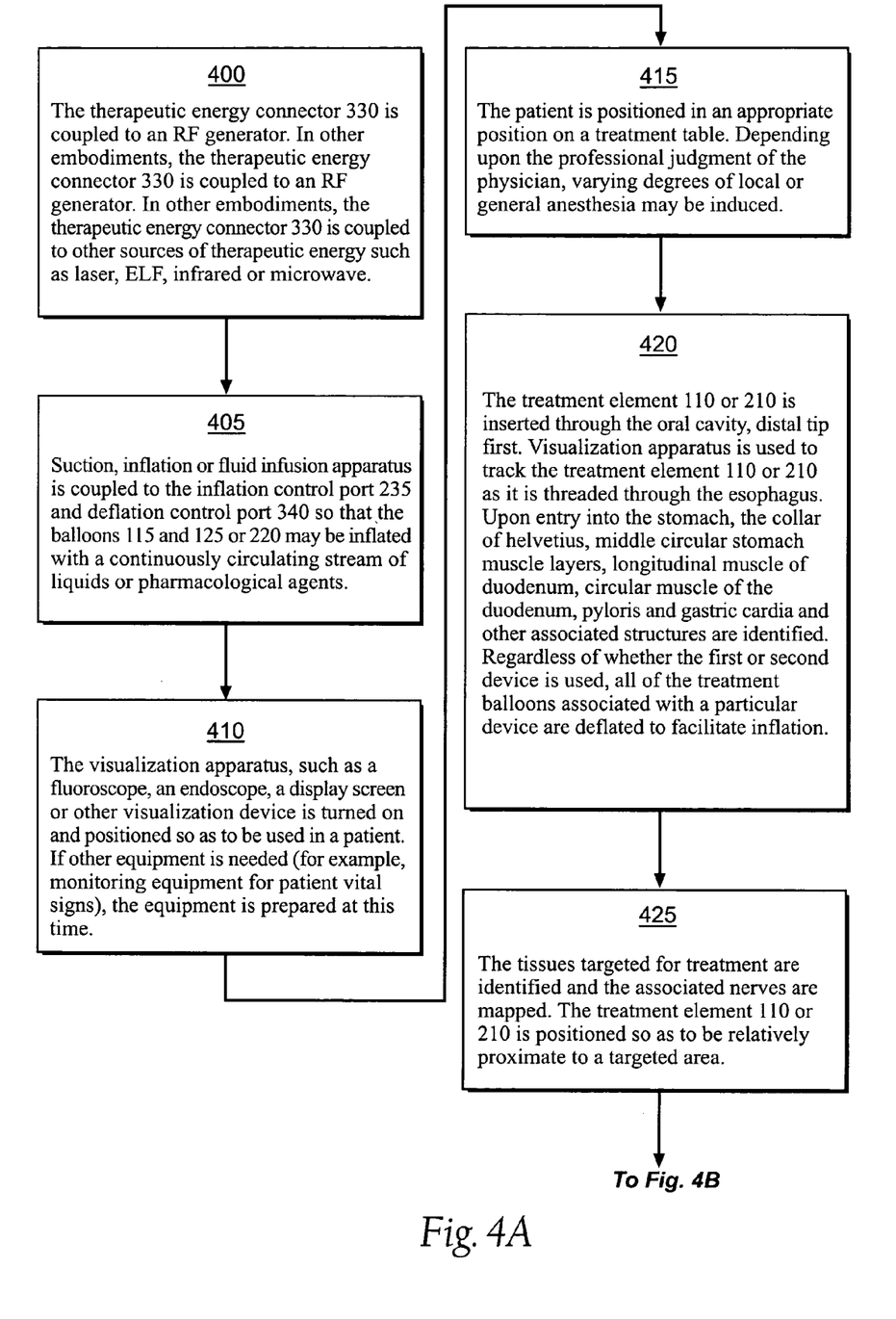
FIGS. 4A and 4B show a process flow diagram of a method for the treatment of obesity.
Figure 4B:
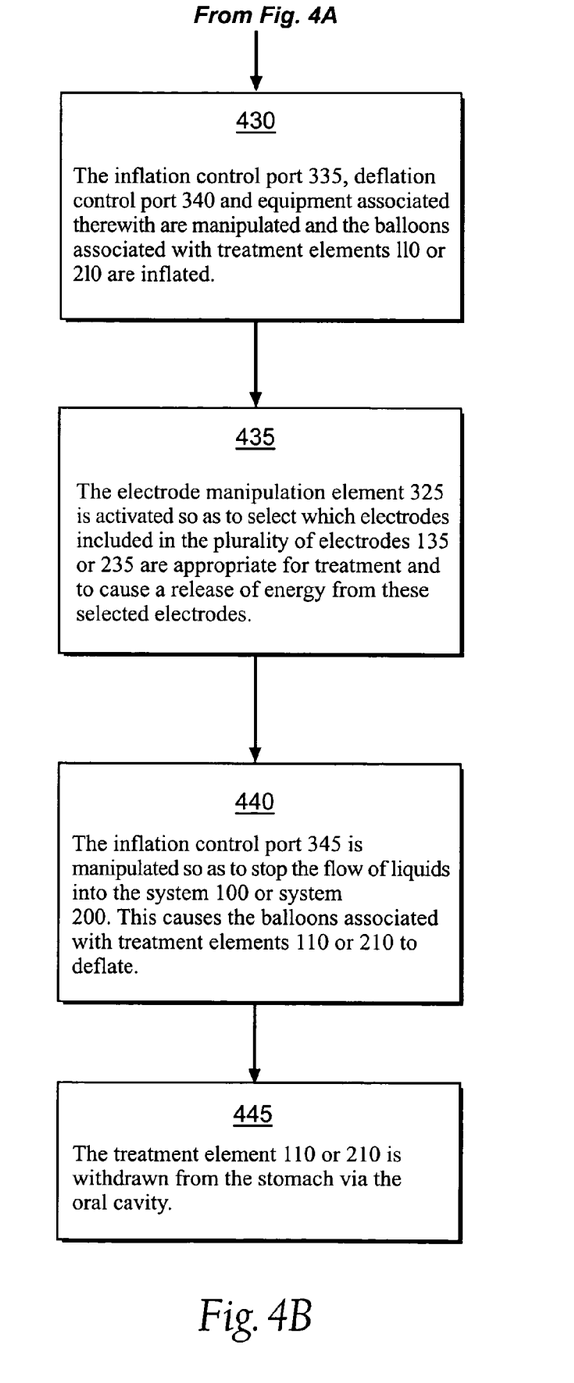

FIGS. 4A and 4B show a process flow diagram of a method for the treatment of obesity.

A method 400 is performed by a system 100 or 200 and a system 300.

At a flow point 400, the therapeutic energy connector 330 is coupled to art RF generator. In other embodiments, the therapeutic energy connector 330 is coupled to an RF generator. In other embodiments, the therapeutic energy connector 330 is coupled to other sources of therapeutic energy such as laser, ELF, infrared or microwave.

At a step 405, suction, inflation or fluid infusion apparatus is coupled to the inflation control port 235 and deflation control port 340 so that the balloons 115 and 125 or 220 may be inflated with a continuously circulating stream of liquids or pharmacological agents. The type of fluid used to inflate the balloons is responsive to the professional judgment of the physician.

At a step 410, the visualization apparatus such as a fluoroscope, an endoscope, a display screen or other visualization device is turned on and positioned so as to be used in a patient. The choice of visualization apparatus and method of use are responsive to judgments by medical personnel. If other equipment is needed (for example, monitoring equipment for patient vital signs), the equipment is prepared at this time.

At a step 415, the patient is positioned on a treatment table, in an appropriate position. Depending upon the professional judgment of the physician, varying degrees of local or general anesthesia may be induced.

At a step 420, the treatment element 110 or 210 is inserted through the oral cavity, distal tip first. Visualization apparatus is used to track the treatment element 110 or 210 as it is threaded through the esophagus. Upon entry into the stomach, the collar of helvetius, middle circular stomach muscle layers, longitudinal muscle of duodenum, circular muscle of the duodenum, pyloris and gastric cardia and other associated structures are identified. Regardless whether the first or second device is used, all of the treatment balloons associated with a particular device are deflated to facilitate inflation.

At a step 425, the tissues targeted for treatment are identified and the associated nerves are mapped. The treatment element 110 or 210 is positioned so as to be relatively proximate to a targeted area.

At a step 430, the inflation control port 335, deflation control port 340 and equipment associated therewith are manipulated and the balloons associated with treatment elements 110 or 210 are inflated from a continuously circulating stream of cooling fluid such as saline, water, Ringers or other liquids. Inflation of the balloon(s) 115 and/or 125, or balloon 220 brings electrodes 135 or electrodes 235 in contact with the targeted tissues. If treatment element 110 is used, balloons 115 and 125 may be inflated dependently or independently of each other. This circulating cooling liquid lowers the relative temperature of the targeted tissue and prevents collateral thermal damage that might otherwise occur. If a microporous balloon(s) is used, the balloon may also be inflated with pharmaceutical agents such as antibiotics, antacids, anti-inflammatories and other drugs including those that might be useful in pretreating the targeted areas. The choice of cooling liquid(s) and pharmaceutical agent(s) are responsive to the professional judgment of the physician.

At a step 435, the electrode manipulation element 325 is activated so as to select which electrodes included in the plurality of electrodes 135 or 235 are appropriate for treatment and to cause a release of energy from these selected electrodes. The duration and frequency of energy are responsive to judgments by medical personnel. This release of energy creates a pattern of lesions in the tissues of the stomach, duodenum and gastric cardia. Depending upon the professional judgment of the physician, energy may be directed toward nerves in the gastric cardia so as to prevent relaxation of stomach muscles. In other embodiments, treatment may include direct modulation of nerves associated with the sensation of satiety or tightening of tissues in portions of the stomach and duodenum that are proximate to each other. This step may be repeated in other portions of the stomach in a manner that is responsive to the professional judgment of the physician. In some embodiments of the invention, the second treatment balloon 125 includes micropores for delivery of liquid to a tissue.

In a preferred embodiment, the temperature increase that accompanies the release of energy from each electrode 135 or 235 is monitored by the thermocouple 136 or 236 associated with that particular electrode in such a way that if the temperature approaches a preset limit, then that particular electrode is automatically deactivated.

At a step 440, the inflation control port 345 is manipulated so as to stop the flow of liquids into the system 100 or system 200. This causes the balloons associated with treatment elements 110 or 210 to deflate.

At a step 445, the treatment element 110 or 210 is withdrawn from the stomach via the oral cavity. In embodiments that involve surgical introduction of the treatment element 110 or 210, the element is removed through the surgical incision. Appropriate follow-up care is responsive to the professional judgment of the physician.

Alternative Embodiments

Although preferred embodiments are disclosed herein, many variations are possible which remain within the concept, scope, and spirit of the invention, and these variations would become clear to those skilled in the art after perusal of this application.

I claim:

1. A method of treating obesity comprising:
providing a treatment device comprising a catheter having a distal end region, a first treatment region on the distal end region sized and configured for deployment in a duodenum, a second treatment region on the distal end region proximal to the first treatment region, the second treatment region being sized and configured for deployment in a stomach, and a spacing region separating the first treatment region from the second treatment region by a distance sized and configured to permit simultaneous deployment of the first treatment region in the duodenum and deployment of the second treatment region in the stomach, the first and second treatment regions each including at least one electrode,
introducing the treatment device into a body region such that the first treatment region is deployed in the duodenum and the second treatment region is at the same time deployed in the stomach,
coupling the at least one electrode on each of the first and second treatment regions to a source of energy, and
delivering energy from the source to the electrodes on the first and second treatment regions to ablate tissue in the stomach and the duodenum.

2. A method as in claim 1
wherein ablating tissue creates a thermal lesion that causes shrinkage of muscle.

3. A method as in claim 1, further comprising:
prior to delivering energy, identifying nerves responsible for relaxation of stomach muscles.

4. A method as in claim 1
wherein the energy delivered is radio frequency energy.

5. A method according to claim 1
wherein the size and configuration of the first treatment region differs from the size and configuration of the second treatment region.

6. A method according to claim 1
wherein energy is delivered simultaneously to the electrodes on the first and second treatment regions to simultaneously ablate tissue in the stomach and the duodenum.

* * * * *